(12) United States Patent
Shalwitz et al.

(10) Patent No.: US 6,309,373 B1
(45) Date of Patent: *Oct. 30, 2001

(54) APPARATUS FOR ALTERING THE CHARACTERISTICS OF A FLUID

(75) Inventors: Robert A. Shalwitz, Columbus; Rhonda L. Cole, Powell; Ronita K. Geckle, Columbus; John J. Kropczynski, Dublin; Terrence B. Mazer, Reynoldsburg; Joseph E. Walton, Westerville, all of OH (US)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/132,888

(22) Filed: Aug. 12, 1998

(51) Int. Cl.[7] ................................................. A61M 37/00
(52) U.S. Cl. .................................. 604/85; 604/91
(58) Field of Search ................................ 604/80–86, 89, 604/91

(56) References Cited

U.S. PATENT DOCUMENTS

| | | | |
|---|---|---|---|
| 1,654,745 | * 1/1928 | Miller | 604/83 |
| 4,390,017 | 6/1983 | Harrison et al. | |
| 4,465,471 | * 8/1984 | Harris et al. | 604/56 |
| 4,479,794 | 10/1984 | Urquhart et al. | |
| 4,511,351 | 4/1985 | Theeuwes | |
| 4,511,353 | 4/1985 | Theeuwes | |
| 4,541,541 | * 9/1985 | Hickman et al. | 220/253 |
| 4,837,111 | 6/1989 | Deters et al. | |
| 4,846,800 | * 7/1989 | Ouriel et al. | 604/4 |
| 4,874,366 | * 10/1989 | Zdeb et al. | |
| 4,968,507 | 11/1990 | Zentner et al. | |
| 4,985,017 | 1/1991 | Theeuwes | |

(List continued on next page.)

FOREIGN PATENT DOCUMENTS

| | | |
|---|---|---|
| 0 151 371 | 8/1985 | (EP) . |
| 0241595 | 10/1987 | (EP) . |
| 0373890 | 12/1989 | (EP) . |
| 2427824 | 1/1980 | (FR) . |
| 9115196 | 10/1991 | (WO) . |
| 9302558 | 2/1993 | (WO) . |

OTHER PUBLICATIONS

R.G. Potts et al., Comparison of Blue Dye Visualization and Glucose Oxidase Test Strip Methods for Detecting Pulmonary Aspiration on Enteral Feedings in Intubated Adults, (1993), Chest, vol. 103, No. 1, pp. 117–121.

Barbara Hopkins, Enteral Nutrition Products, (1994), Mosby–Year Book, Inc., pp. 439–467 (Chapter 24).

*Primary Examiner*—Sharon Kennedy
*Assistant Examiner*—Catherine Serke
(74) *Attorney, Agent, or Firm*—Brain R. Woodworth

(57) ABSTRACT

An apparatus for altering characteristics of a fluid. The apparatus includes a canister having a side wall, a first end wall, and a second end wall defining a chamber therein. A beneficial agent is disposed in the chamber. The end walls define apertures therethrough. The apparatus further includes a tubing portion defining a first end portion constructed for connection to a fluid source and an outlet portion. The tubing portion also defines a canister-receiving portion intermediate the first end portion and the outlet portion. The canister-receiving portion defines a first fluid flow channel fluidly connecting the first end portion and the second outlet portion of said tubing portion. The canister-receiving portion also defines first and second fluid flow orifices therethrough. The canister-receiving portion is constructed to be selectively connectable to the canister such that fluid from the tubing portion can be selectively directed through the canister chamber, thereby causing the beneficial agent to become dispersed in the flowing fluid.

16 Claims, 2 Drawing Sheets

U.S. PATENT DOCUMENTS

| | | |
|---|---|---|
| 5,024,657 * | 6/1991 | Needham et al. .................... 604/85 |
| 5,069,671 | 12/1991 | Theeuwes . |
| 5,147,646 | 9/1992 | Graham . |
| 5,160,742 | 11/1992 | Mazer et al. . |
| 5,162,057 | 11/1992 | Akiyama et al. . |
| 5,318,558 | 6/1994 | Linkwitz et al. . |
| 5,385,547 | 1/1995 | Wong et al. . |
| 5,520,307 * | 5/1996 | Miller et al. ............................ 221/2 |
| 5,651,359 | 7/1997 | Bougamont et al. . |

* cited by examiner

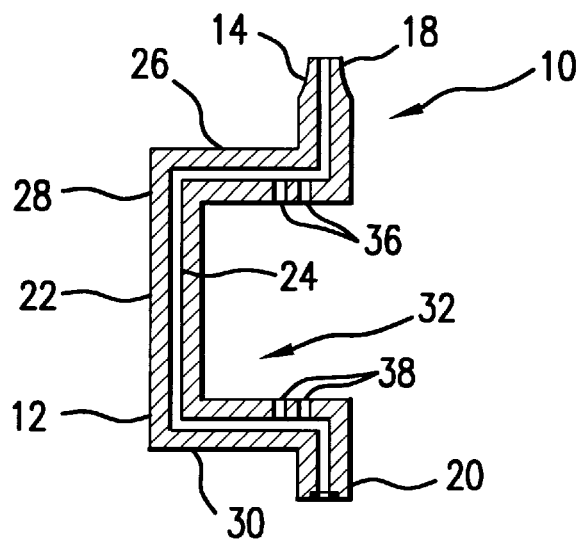
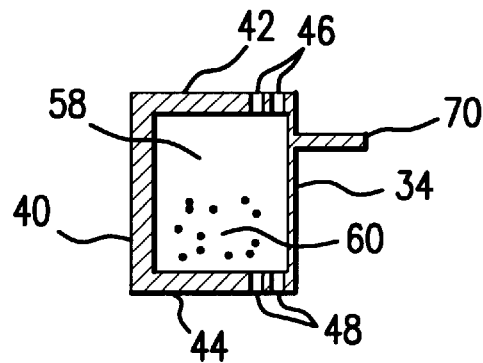
FIG.2     FIG.3
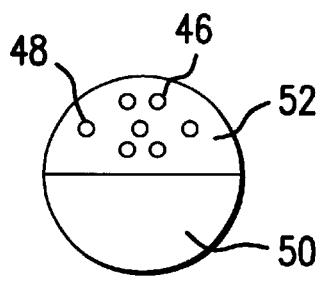
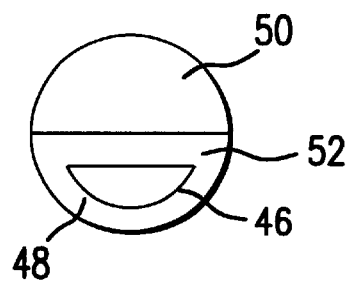
FIG.4     FIG.5
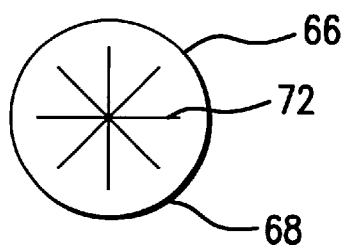
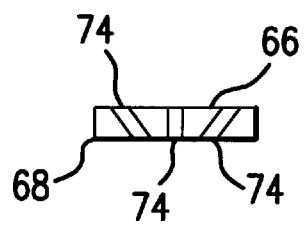
FIG.6     FIG.7

APPARATUS FOR ALTERING THE CHARACTERISTICS OF A FLUID

BACKGROUND OF THE INVENTION

The present invention is directed to an apparatus for altering the characteristics of a fluid. In particular, the present invention is directed to an apparatus defining a first flow path and a second flow path. When the fluid follows the first flow path, it reaches an output of the apparatus without an alteration of its characteristics. When the fluid follows the second flow path, the fluid passes through a chamber containing a beneficial agent such that the beneficial agent becomes dispersed in the flowing fluid, thereby altering the fluid's characteristics. The apparatus is constructed such that flow through the second flow path can be selectively controlled.

The delivery of enteral and parenteral products to a patient from a fluid source is well known. Such fluid products can be provided in hangable containers such as bottles and flexible bags having a bottom outlet that is fluidly connected to a drip chamber. The drip chamber in turn is fluidly connected to a flexible tube which in turn delivers the enteral or parenteral product to a patient. For example, an enteral product can be delivered to a patient by way of a nasogastric tube or a feeding tube inserted through a gastrostomy or a jejunostomy while a parenteral product can be delivered by way of a catheter inserted into a patient's vascular system. The parenteral or enteral product is delivered from the container to the patient through the use of gravity or through the use of an infusion pump. Pumps useful in the administration of enteral and parenteral products are well known and include, but are not limited to, rotary peristaltic pumps, piston pumps, and cassette pumps.

Although such parenteral and enteral fluid delivery systems have been used widely in the medical field for many years, they lack a degree of flexibility. That is, in some cases it is desirable to supplement or otherwise alter the contents of enteral or parenteral products with an additional agent or with additional quantities of an agent already contained in the product. Such supplementation or alteration typically requires the use of a specialized delivery system. For example, a piggy-back delivery system can be used in order to provide a bolus of the additional agent to the enteral or parenteral product during administration thereof. Other known sets capable of simultaneously delivering a plurality of fluids from a plurality of sources can be used. However, such systems include additional tubes and ports that can become entangled during use. Further, such systems are typically higher in cost due to the need for additional lengths of tubing and Y-connectors.

Some fluid delivery systems provide for supplementation of the liquid product in a container by providing a port on the container that can be opened, thereby permitting an additional agent, or additional quantities of an agent contained in the product, to be added directly thereto. However, by allowing such direct access to the product, the sterility of the product may be compromised. In the case of parenteral products, sterility must be maintained during delivery to a patient, thus making direct access unacceptable for parenteral products. The sterility of enteral products historically has posed less of a concern to medical professionals. However, there is a growing recognition of the desirability of providing and delivering enteral nutritional products to patients aseptically. Accordingly, it is desirable to provide a method and apparatus for modifying the characteristics of enteral and parenteral products without exposing the products to contamination.

Without a system or apparatus for easily supplementing the contents of a liquid product prior to delivery thereof from a container to a patient, it becomes necessary to provide products having a wider variety of dosages, volumes, and combinations of agents. For this reason, delivery systems such as those described in U.S. Pat. Nos. 4,511,353; 5,318,558; and 5,324,280 have been developed. In these systems, an agent to be delivered parenterally to a patient is contained in a capsule from which it is ejected over time as a result of osmotic infusion. That is, as the capsule is subjected to the presence of a fluid, the contents of the capsule are released into the fluid. U.S. Pat. No. 5,318,558 discloses the use of such a system in the delivery of agents directly into the body by exposing the capsule directly to bodily fluids.

U.S. Pat. No. 5,069,071 describes a formulation chamber in which various forms of sustained release mechanism can be employed to release agents into a parenteral fluid traversing through the formulation chamber, thereby providing for delivery of the supplemental agent to the patient.

In each of the systems disclosed in the above-referenced patents, it is necessary to place the additional, beneficial agent(s) in the flow path of a tubing set prior to delivering fluid to a patient through the tubing set. Thus, in order to delay the introduction of one or more beneficial agents into the flowing fluid, it was necessary to formulate the beneficial agents such that they had a delayed release into the fluid, thereby increasing the cost of formulating the beneficial agent. It is desirable to provide an apparatus that allows for the introduction of beneficial agents in varying amounts and at various times without the need for formulating the beneficial agents such that their release into the flowing fluid is delayed. It also is desirable to provide an apparatus that allows an operator to initiate the introduction of one or more beneficial agents into the flowing fluid on an as-needed basis without the need for opening the apparatus to an external environment thereof.

SUMMARY OF THE INVENTION

The present invention provides an apparatus for altering characteristics of a fluid flowing therethrough. The apparatus includes a canister having a side wall, a first end wall, and a second end wall defining a chamber therein. A beneficial agent is disposed in the chamber. The end walls define apertures therethrough. The apparatus further includes a tubing portion defining a first end portion constructed for connection to a fluid source and an outlet portion. The tubing portion also defines a canister-receiving portion intermediate the first end portion and the outlet portion. The canister-receiving portion defines a first fluid flow channel fluidly connecting the first end portion and the second outlet portion of said tubing portion. The canister-receiving portion also defines first and second fluid flow orifices therethrough. The canister-receiving portion is constructed to be selectively connectable to the canister such that fluid from the tubing portion can be selectively directed through the canister chamber, thereby causing the beneficial agent to become dispersed in the flowing fluid.

BRIEF DESCRIPTION OF THE DRAWINGS

For a more complete understanding of the present invention, reference may be had to the following Detailed Description read in connection with the accompanying drawings in which:

FIG. 2 is a cross-sectional view of an apparatus for altering characteristics of a fluid in accordance with one embodiment of the present invention;

FIG. 3 is a cross-sectional view of a canister in accordance with one embodiment of the present invention;

FIG. 4 is an end view of a canister in accordance with a first embodiment of the present invention;

FIG. 5 is an end view of a canister in accordance with a second embodiment of the present invention;

FIG. 6 is an end view of a canister in accordance with a third embodiment of the present invention;

FIG. 7 is a cross-sectional view of an end wall of the canister constructed in accordance with the third embodiment of the present invention after application of a predetermined force thereto.

DETAILED DESCRIPTION

Figure 8:
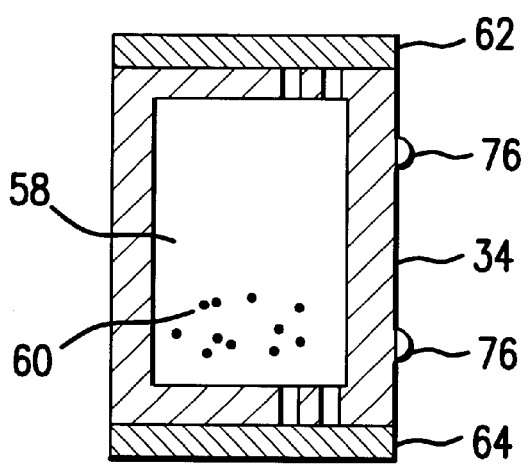
FIG. 8 is a cross-sectional view of a canister in accordance with an alternative embodiment of the present invention.

The present invention is directed to an apparatus for altering the characteristics of a fluid. For the purposes of this disclosure, the apparatus will be described in the context of an enteral nutritional fluid delivery system. However, it will be appreciated that the present invention also can be used to alter the characteristics of a parenteral fluid as it is delivered to a patient.

The present invention is described herein with reference to the accompanying figures. Terms of reference such as "upper" and "lower" are used to facilitate an understanding of the present invention in view of the accompanying figures. These terms are not intended to be limiting and one of ordinary skill in the art will recognize that the present invention can be practiced in a variety of spatial orientations without departing from the spirit and scope of the present invention.

As used herein, the terms "enteral nutritional product" and "enteral product" refer to a liquid composition designed to be delivered to a patient's gastrointestinal tract. Delivery to the gastrointestinal tract can be effected through a nasogastric tube, through a gastrostomy tube, and/or through a jejunostomy tube. These liquids typically have a viscosity of at least about 3 centipoises.

A "beneficial agent" is an agent that is, or that is believed to be, nutritionally or pharmaceutically important to the patient, or that is otherwise medically important as in the case of a probiotic, or that serves as a diagnostic agent as in the case of an opaquing agent, an imaging agent, or a coloring agent.

A "probiotic" is understood to be a live microbial food supplement that beneficially affects the human host by improving the microbial balance in the host's gastrointestinal tract, e.g., *Lactobacillus reuteri*.

A "useful amount" of a beneficial agent is an amount that is physiologically effective or diagnostically detectable when administered to a patient or that is believed to be physiologically effective or diagnostically detectable when administered to a patient. That is, an amount that is reasonably expected to produce a detectable effect on the patient on either a short term or long term basis when delivered to the patient or an amount that is detectable in diagnosing a disease state or a medical condition.

"At least one beneficial agent" is meant to refer to the singular as well as the plural and is intended to include combinations of ingredients, agents, or factors.

The term "dispersible" as used herein with respect to beneficial agents is to be understood to apply to substances that are soluble as well as those that are suspendable enough to be taken up readily and carried along by the liquid medium as the liquid flows through the chamber containing the beneficial agent. Dispersible agents include, but are not limited to, agents in controlled release dosage form.

The term "feeding set" refers to a combination of known elements useful in delivering a product from a liquid container to a patient. Such combinations include, but are not intended to be limited to, combinations comprising one or more of drip chambers, formulation chambers, lengths of tubing, flow control clamps, pumps, and other devices commonly found in infusion sets.

The term "infusion" is meant to refer to the enteral or parenteral delivery of a liquid to a patient.

The term "flowing the fluid" is intended to include the utilization of gravity to effect flow as well as the utilization of a pump of known construction to effect flow.

Figure 1:
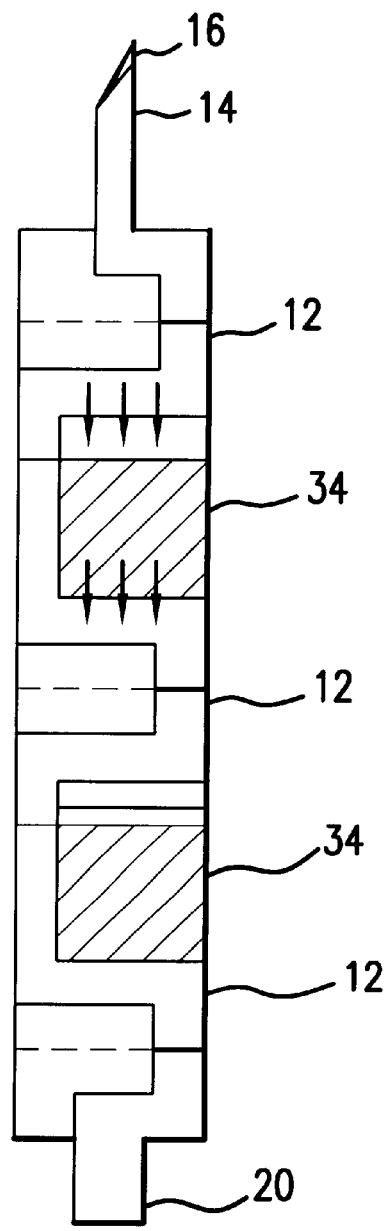
FIG. 1 is a schematic view of two, interconnected units of the apparatus for altering characteristics of a fluid in accordance with one embodiment of the present invention.

An apparatus for altering characteristics of a fluid is generally indicated at 10 in FIG. 2. Apparatus 10 includes a tubing portion 12 having a first end portion 14 constructed to be connected to a fluid source. As depicted in FIG. 1, first end portion 14 is configured as a spike 16 of known construction for piercing a membrane seal on a fluid container of the type typically used in the medical field. As depicted in FIG. 2, first end portion 14 is configured as a male luer member 18 constructed for frictional retention within a complementary female luer member provided on a fluid source. It will be appreciated that first end portion 14 can have any number of other configurations that facilitate connection of first end portion 14 to a fluid source. For example, first end portion 14 can be constructed for connection to a fluid source by way of a locking luer connection or by way of a threaded connection. Further, first end portion 14 can be constructed to be frictionally connected to a fluid source by way of, for example, a snap fitment of known construction. Other known mechanisms for connection of tubing portion 12 to a fluid source are intended to be within the scope of the present invention.

Tubing portion 12 further includes an outlet portion 20 which, in the embodiment depicted in FIG. 1, is constructed to deliver fluid from tubing portion 12 to a separate fluid delivery apparatus, e.g., a length of tubing constructed to deliver an enteral or parenteral fluid to a patient. In the embodiment of the invention depicted in FIG. 1, outlet portion 20 has a female luer configuration such that it can be frictionally connected to a male luer member, e.g., male luer member 18 of first end portion 14. In this way, multiple tubing portions 12 can be interconnected, as discussed in greater detail herein. However, it will be appreciated that outlet portion 20 can have a variety of known constructions, as above-discussed with respect to first end portion 14.

Tubing portion 12 further includes canister-retaining portion 22, as depicted in FIG. 1. Canister-receiving portion 22 is positioned intermediate first end portion 14 and outlet portion 20. Canister-retaining portion 22, first end portion 14, and outlet portion 20 define a first fluid flow channel 24 therethrough. It will be appreciated that first fluid flow channel 24 provides for fluid communication through tubing portion 12 from first end portion 14 to outlet portion 20 such that fluid can flow through tubing portion 12. As depicted in the accompanying figures, tubing portion 12 is of a unitary construction and is made of a material commonly used in the delivery of enteral and parenteral fluids to a patient. However, it is to be appreciated that tubing portion 12 can be constructed of several distinct pieces without departing from the scope of the present invention.

In the embodiment of the present invention depicted in the FIG. 2, canister-receiving portion 22 includes a first segment 26, second segment 28, and third segment 30. First segment 26 and third segment 30 are substantially parallel and define a canister-retention space 32 therebetween. Canister-retention space 32 is further defined by second segment 28 which, in the depicted in embodiment, is substantially perpendicular to first segment 26 and third segment 30. It will be appreciated that the relative orientations of first segment 26, second segment 28, and third segment 30 can be varied without departing from the scope of the present invention. First segment 26, second segment 28, and third segment 30 can be constructed and oriented to define canister-retention spaces 32 having a wide variety of configurations. In this way, canister-retention space 32 can be constructed to match the configuration of a canister 34 to be placed therein. This construction can serve to prevent the insertion of an improper canister 34 into canister-retention space 32, thereby ensuring that canisters 34 containing improper beneficial agents are not placed into the flow path of a feeding set that includes apparatus 10 of the present invention.

First segment 26 of canister-retaining portion 22 defines one or more first fluid flow orifices 36 therethrough. Third segment 30 of canister-retaining portion 22 defines one or more second fluid flow orifices 38 therethrough. First and second fluid flow orifices 36, 38 preferably are oriented such that they provide fluid communication between first fluid flow channel 22 and canister-retaining space 32.

Canister 34 includes a side wall 40, a first end wall 42, and a second end wall 44. In the embodiment of the present invention depicted herein, canister 34 is substantially cylindrical. However, it is to be appreciated that canister 34 can have a variety of shapes and sizes without departing from the scope of the present invention. For example, canister 34 can be substantially spherical in shape. Further, the shape of canister 34 and the shape of canister-retaining space 32 can be selected so as to prevent certain shapes of canisters 34 from being placed in certain canister-retaining spaces 32, thereby limiting the possibility that apparatus 10 of the present invention can be used inappropriately.

First end wall 42 defines one or more apertures 46 therethrough. Second end wall 44 defines one or more apertures 48 therethrough. FIGS. 4 and 5 represent alternative configurations for both first end wall 42 and second end wall 44. In one embodiment of the present invention depicted in FIGS. 4 and 5, first end wall 42 and second end wall 44 include a first, substantially imperforate section 50 and a second section 52. In the embodiment depicted in FIG. 4, a plurality of apertures 46, 48 are defined by second section 52. In the embodiment depicted in FIG. 5, a single aperture 46, 48 is defined by second section 52. It will be appreciated that the configurations of first end wall 42 and second end wall 44 can be varied from those depicted herein, and varied from one another, without departing from the scope of the present invention.

Canister 34 is constructed such that it can be received by canister-retention space 32, that is, such that first fluid flow orifice 36 defined by first segment 26 of canister-retaining portion 22 is in fluid communication with aperture 46 defined by first end wall 42 and such that second fluid flow orifice 38 defined by third segment 30 of canister-retaining portion 22 is in fluid communication with aperture 48 defined by second end wall 44.

In a preferred embodiment of the present invention, canister 34 is constructed to be received by canister-retention space 32 such that canister 34 is rotatable relative to canister-retaining portion 22 of tubing portion 12. In a first configuration of the preferred embodiment, canister 34 is substantially cylindrical in shape. It will be appreciated that the cylindrical shape of canister 34 will facilitate relative rotation between canister 34 and canister-retaining portion 22 because side wall 40 of canister 34 does not have any corners to impede such rotation. In an alternative configuration of the preferred embodiment of the present invention, first end wall 42, or a portion thereof, is rotatable relative to side wall 40 of canister 34. In this embodiment, second end wall 44, or a portion thereof, also is rotatable relative to side wall 40 of canister 34.

In the preferred embodiment of the present invention, canister 34 is rotatable between a first position and a second position. In the second position, first fluid flow orifice 36 defined by first segment 26 of canister-retaining portion 22 is in direct contact with first, substantially imperforate section 50 of first end wall 42 and second fluid flow orifice 38 defined by third segment 30 of canister-retaining portion 22 is in direct contact with first, substantially imperforate section 50 of second end wall 44. Canister 34 and canister-retaining portion 22 preferably are configured such that substantially no fluid is released through first and second fluid flow orifices 36, 38 when canister 34 is in the second position. Accordingly, it is preferred that first and second end walls 42, 44 be constructed to substantially seal first and second fluid flow orifices 36, 38, respectively. For example, first, substantially imperforate sections 50 of first and second end walls 42, 44 can have an elastomeric surface constructed to provide a substantially fluid-tight seal of first and second fluid flow orifices 36, 38. It also will be appreciated that a relatively tight fit between first end wall 42 and first segment 26 and between second end wall 44 and third segment 30 is desirable in order to facilitate the desired sealing of first and second fluid flow orifices 36, 38. That is, a length of canister 34 from first end wall 42 to second end wall 44 preferably is substantially the same as the distance from first segment 26 to third segment 30 across canister-retention space 32. When canister 34 is in its first position relative to canister-retaining portion 22 of tubing portion 12, a fluid introduced into first end portion 14 of tubing portion 12 flows through first fluid flow channel 24 to outlet portion 20 of tubing portion 12.

When canister 34 is in its first position relative to canister-retaining portion 22 of tubing portion 12, first and second fluid flow orifices 36, 38 are in fluid communication with apertures 46, 48 defined through second sections 52 of first end wall 42 and second end wall 44, thereby allowing fluid to flow from first fluid flow channel 24 through canister 34. Here again it will be appreciated that a relatively close fit between canister 34 and first and third segments 26, 30 is desirable in order to prevent the flow of fluid outside of apparatus 10.

Canister 34 preferably defines chamber 58 therein. At least one beneficial agent 60 is positioned within chamber 58. Beneficial agents 60 are formulated to be dispersible in a fluid flowing through chamber 58 defined by canister 34. Beneficial agents 60 can be in tablet form, powder form, liquid form, gel form, or any other known form. Beneficial agents 60 can be placed in chamber 58 defined by canister 34 either by a manufacturer or by a pharmacist or other individual immediately prior to use of apparatus of the present invention.

Because beneficial agent 60 is selected to be dispersible in a particular fluid flowing through chamber 58 during use of apparatus 10 of the present invention, beneficial agent 60 will be dispersed in a fluid exiting outlet portion 20 of tubing portion 12 when canister 34 is in its first position relative to canister-retaining portion 22 of tubing portion 12. It will be appreciated that it is desirable that a useful amount of beneficial agent 60 be present in the fluid exiting outlet portion 20. In this regard, apertures 46, 48 defined by first and second end walls 42, 44, and first and second fluid flow orifices 36, 38 defined by first and third segments 26, 30, preferably are dimensioned so as to ensure that an adequate amount of fluid flowing through tubing portion 12 flows through chamber 58, thereby exposing beneficial agent 60 to an adequate amount of the flowing fluid. It will be appreciated that the preferred dimensions of apertures 46, 48 and fluid flow orifices 36, 38 will be dependent upon a variety of factors including, but not limited to, the fluid to be flowed through tubing portion 12, the rate at which fluid is to be flowed through tubing portion 12, the formulation of the beneficial agent 60, the beneficial agent 60, and the desired delivery rate of beneficial agent 60.

In the above-referenced second configuration of the preferred embodiment of the present invention, first and second end walls 42, 44, or portions thereof, are rotatable between the first and second positions described above with respect to the first configuration of the preferred embodiment of the present invention. That is, in the first position, apertures 46, 48 defined respectively by first end wall 42 and second end wall 44 are in fluid communication with first and second fluid flow orifices 36, 38, while in the second position, apertures 46, 48 are not in fluid communication with first and second fluid flow orifices 36, 38.

In an alternative embodiment of the present invention depicted in FIG. 8, seals 62, 64 are provided. Seals 62, 64 serve to seal fluidly apertures 46, 48 from first and second fluid flow orifices 36, 38. Seals 62, 64 can be mounted on first segment 26 and third segment 30 of canister-retaining portion 22, or, as depicted in FIG. 8, on first end wall 42 and second end wall 44 of canister 34. Alternatively, seals 62, 64 can be separate elements from both canister-retaining portion 22 and canister 34. Seals 62, 64 are constructed such that they can be selectively deactivated or removed in order to provide fluid communication between apertures 46, 48 and first and second fluid flow orifices 36, 38. For example, seals 62, 64 can be in the form of a sheet of fluid-impervious material which, when used in connection with apparatus 10 of the present invention, prevents fluid flow through fluid flow orifices 36, 38.

In one configuration of the above-discussed embodiment, sealing members 66, 68 form first end wall 42 and second end wall 44, respectively, of canister 34, as depicted generally in FIGS. 6 and 7. Sealing members 66, 68 are constructed of a known, frangible material that breaks upon the application of an external force of a predetermined magnitude, e.g., a radially inwardly directed force, in order to provide a flow channel(s) therethrough, thus providing fluid communication between apertures 46, 48 and first and second fluid flow orifices 36, 38 through the newly-formed flow channel(s). In the embodiment depicted in FIGS. 6 and 7, sealing members 66, 68 are scored, as indicated by reference numeral 72, in order to facilitate breaking thereof upon the application of a radially inwardly directed force. Upon the application of such a force to the embodiment depicted in FIGS. 6 and 7, channels 74 are defined through However, it will be appreciated that a variety of other configurations of sealing members 66, 68 are possible without departing from the scope of the present invention.

Canister 34 and canister-retaining portion 22 preferably are configured such that canister-retaining portion 22 retains canister 34 therein after canister 34 has been connected to canister-retaining portion 22, thereby preventing leakage of fluid from apparatus 10. In the embodiment depicted in the accompanying figures, canister 34 is configured to be frictionally retained within canister-retention space 32 by canister-retaining portion 22. It will be appreciated that a variety of other locking configurations are possible for the retention of canister 34 in canister-retention space 32, including, but not limited to, threaded connections, snap-fit connections, and other known locking arrangements.

Canister 34, first segment 26, and third segment 30 can be configured such that canister 34 can only be rotated in one direction relative to canister-retaining portion 22. In addition, lever 70 can be provided on canister 34 in order to facilitate rotation of canister 34 relative to canister-retaining portion 22. In those embodiments of the present invention in which first end wall 42 and second end wall 44 are rotatable relative to side wall 40, lever 70 can be connected to either side wall 40 or to first and second end walls 42, 44 in order to facilitate relative rotation therebetween.

Canister 34 and canister-retaining portion 22 also may include indicia 76 thereon in order to indicate when canister 34 is in its first, activated position and when canister 34 is in its second, inactivated position. Indicia 76 can have a variety of forms, including raised markings provided on an exterior surface of canister 34, as depicted in FIG. 8. Indicia 76 can have a variety of other forms, including raised markings provided on tubing portion 12, colorations provided on canister 34 and/or tubing portion 12, and other markings and indicators of known construction.

In order to use apparatus 10 of the present invention, one or more tubing portions 12 are provided. The tubing portions 12 are connected to one another by connecting the outlet portion 20 of an upper tubing portion 12 to a first end portion 14 of a lower tubing portion. For each tubing portion 12, a canister 34 preferably is provided. The canisters 34 are selected based upon the beneficial agent 60 contained therein, per the needs of a patient to whom fluid is to be delivered. The canisters 34 are placed in respective canister-retention spaces 32 defined by tubing portions 12 such that canisters 34 are in their second, closed position, thereby preventing the flow of fluid from first fluid flow channel 24 through chamber 58. The resulting structure is then ready for placement in fluid communication with a feeding set. For example, first end portion 14 of the uppermost tubing portion 12 can be fluidly connected to a fluid source of known construction, e.g., a feeding tube, a flexible container, or a rigid container. This fluid connection can be effected in a variety of ways, including the use of spike 16 or male luer member 18, dependent upon the configuration of the fluid source. The outlet portion 20 of the lowermost tubing portion 12 can be connected to a fluid delivery device of known construction for delivery of a fluid to a patient.

After a feeding set including apparatus 10 of the present invention has been connected to a fluid source and to a patient, fluid can be directed through apparatus 10 of the present invention, i.e., through first fluid flow channel 24. At a preselected time, one or more of the canisters 34 can be moved from their second to their first positions relative to tubing portion 12, thereby causing fluid to flow through chambers 58 of the "activated" canisters 34. It may be preferable to construct canisters 34 and tubing portion 12 such that canisters 34 cannot be returned to their second positions after they have been "activated", i.e., placed in their first position. This feature, in combination with indicia 76, will prevent confusion regarding whether or not a particular canister 34 has been activated. It will be appreciated that canisters 34 can be activated at different times, per the needs of the individual patient to whom fluid is being delivered. It further will be appreciated that beneficial agents 60 contained in chambers 58 of activated canisters 34 will become dispersed in the fluid flowing therethrough and thus delivered to the patient.

Upon completion of a regimen of fluid delivery to a patient, apparatus 10 of the present invention can be detached from the feeding set and discarded, or, in the alternative, sterilized and re-used.

Although the present invention has been described herein in connection with certain preferred embodiments, one of ordinary skill will appreciate that various modifications are possible without departing from the intended spirit and scope of the invention which is defined by the appended claims.

What is claimed is:

1. An apparatus for altering characteristics of a fluid, said apparatus comprising:

a canister comprising a side wall, a first end wall, a second end wall, said first and second end walls each defining at least one aperture therethrough, said canister defining a chamber therein, said chamber in fluid communication with said apertures defined by said first and second end walls, said first end wall having a first section and a second section, said first section of said first end wall being substantially imperforate, said second section of said first end wall defining said aperture therethrough, said second end wall having a first section and a second section, said first section of said second end wall being substantially imperforate, said second section of said second end wall defining said aperture therethrough;

a beneficial agent disposed within said chamber defined by said canister; and a tubing portion, said tubing portion including a first end portion constructed for connection to a fluid source, said tubing portion further including an outlet portion and a canister-receiving portion intermediate said first end portion and said outlet portion, said canister-receiving portion having a first fluid flow channel fluidly connecting said first end portion and said outlet portion of said tubing portion, said canister-receiving portion having defined therethrough a first fluid flow orifice and a second fluid flow orifice at a position spaced from said first fluid flow orifice, each of said first and second fluid flow orifices providing fluid communication between said first fluid flow channel and an external environment of said first fluid flow channel defined by said canister-receiving portion, said canister-receiving portion constructed to receive said canister with said aperture defined through said first end wall of said canister being selectively connectable for fluid communication with said first fluid flow orifice defined by said canister-receiving portion of said tubing portion, and said aperture defined by said second end wall of said canister being selectively connectable for fluid communication with said second fluid flow orifice defined by said canister-receiving portion of said tubing portion, at least a portion of fluid flow through said tubing portion being directed through said chamber defined by said canister when said canister is received by said canister-receiving portion of said tubing portion and said apertures are selectively connected with said first and second fluid flow orifices;

said canister being rotatable relative to said canister-receiving portion of said tubing portion when said canister is received by said canister-receiving portion, said canister being rotatable between a first position in which said first and second fluid flow orifices are in fluid communication with said apertures defined by said second sections of said first and second end walls, respectively, and a second position in which said first sections of said first and second end walls are aligned with said first and second fluid flow orifices, respectively, to prevent fluid flow therethrough.

2. An apparatus for altering characteristics of a fluid in accordance with claim 1, wherein said canister has indicia on an exterior surface thereof, said indicia indicating when said canister is in said first position relative to said canister-retaining portion and when said canister is in said second position relative to said canister-retaining portion.

3. An apparatus for altering characteristics of a fluid in accordance with claim 1, wherein said first and second end walls of said canister are moveable relative to said side wall of said canister and relative to said canister-receiving portion of said tubing portion when said canister is received by said canister-receiving portion, said first and second end walls being moveable between a first position in which said first and second fluid flow orifices are in fluid communication with said apertures defined by said first and second end walls, respectively, and a second position in which said first and second fluid flow orifices are out of alignment with said apertures defined by said first and second end walls to prevent fluid flow therethrough.

4. An apparatus for altering characteristics of a fluid in accordance with claim 1, wherein said apparatus further comprises a first seal fluidly sealing said aperture defined by said first end wall from said first flow orifice, said first seal constructed to be selectively removable from said apparatus when said canister is connected to said canister-receiving portion of said tubing portion.

5. An apparatus for altering characteristics of a fluid in accordance with claim 4, wherein said apparatus further comprises a second seal fluidly sealing said aperture defined by said second end wall from said second flow orifice, said second seal constructed to be selectively removable from said apparatus when said canister is connected to said canister-receiving portion of said tubing portion.

6. An apparatus for altering characteristics of a fluid in accordance with claim 1, wherein said first end wall of said canister defines a plurality of apertures therethrough.

7. An apparatus for altering characteristics of a fluid in accordance with claim 1, wherein said apparatus further comprises a first seal fluidly sealing said aperture defined by said first end wall from said first flow orifice, said first seal constructed of a frangible material, whereby said first seal forms a flow channel therethrough upon application of a predetermined force thereto.

8. An apparatus for altering characteristics of a fluid in accordance with claim 7, wherein said apparatus further comprises a second seal fluidly sealing said aperture defined by said second end wall from said second flow orifice, said second seal constructed of a frangible material, whereby said second seal forms a flow channel therethrough upon application of a predetermined force thereto.

9. An apparatus for altering characteristics of a fluid in accordance with claim 1, wherein the first section of the first and second end walls, respectively, has an elastomeric surface to provide a substantially fluid tight seal when the canister is in the second position.

10. An apparatus for altering characteristics of a fluid in accordance with claim 1, wherein the canister is rotatable in only one direction.

11. An apparatus for altering characteristics of a fluid, said apparatus comprising:

a canister comprising a side wall, a first end wall, and a second end wall, said first and second end walls each defining at least one aperture therethrough, said canister defining a chamber therein, said chamber in fluid communication with said apertures defined by said first and second end walls, said first end wall having a first section and a second section, said first section of said first end wall being substantially imperforate, said second section of said first end wall defining said aperture therethrough, and wherein said second end wall has a first section and a second section, said first section of said second end wall being substantially imperforate, said second section of said second end wall defining said aperture therethrough;

a beneficial agent disposed within said chamber defined by said canister, said beneficial agent being dispersible in a fluid flowing through said chamber defined by said canister;

a tubing portion including a first end portion constructed for connection to a fluid source, said tubing portion further including an outlet portion and a canister-receiving portion intermediate said first end portion and said outlet portion, said canister-receiving portion defining a first fluid flow channel fluidly connecting said first end portion and said outlet portion of said tubing portion, said canister-receiving portion having a first segment extending from said first end portion at a first angle, said first segment defining at least one first fluid orifice therethrough;

a second segment extending from said first segment at a second angle; and a third segment extending from said second segment at a third angle, said third segment defining at least one second fluid orifice therethrough; and said first and third segments configured to engage, respectively, said first end wall and said second end wall of said canister when the canister is received therebetween; and said first and second fluid orifices being selectively connectable to communicate fluidly with said apertures defined by said first and second end walls of said canister when said canister is received by said canister-receiving portion of said tubing portion;

said canister being rotatable relative to said canister-receiving portion of said tubing portion when said canister is received by said canister-receiving portion, said canister being rotatable between a first position in which said first and second fluid flow orifices are in fluid communication with said apertures defined by said second section of said first and second end walls, respectively, and a second position in which said first section of said first and second end walls are aligned with said first and second fluid flow orifices, respectively, to prevent fluid flow therethrough.

12. An apparatus for altering characteristics of a fluid in accordance with claim 11, wherein said first and third segments of said canister-receiving portion have respective first and third longitudinal axes, and wherein said first and third longitudinally axes are substantially parallel.

13. An apparatus for altering characteristics of a fluid in accordance with claim 11, wherein said first, second, and third angles are each substantially 90°.

14. An apparatus for altering characteristics of a fluid in accordance with claim 11, wherein said first and second end walls of said canister are moveable relative to said side wall of said canister and relative to said canister-receiving portion of said tubing portion when said canister is received by said canister-receiving portion, said first and second end walls being moveable between a first position in which said first and second fluid flow orifices are in fluid communication with said apertures defined by said first and second end walls, respectively, and a second position in which said first and second fluid flow orifices are out of alignment with said apertures defined by said first and second end walls to prevent fluid flow therethrough.

15. An apparatus for altering characteristics of a fluid in accordance with claim 11, wherein the first section of the first and second end walls, respectively, has an elastomeric surface to provide a substantially fluid tight seal when the canister is in the second position.

16. An apparatus for altering characteristics of a fluid in accordance with claim 10, wherein the canister is rotatable in only one direction.

* * * * *